US012268543B2

(12) United States Patent
Wentland

(10) Patent No.: US 12,268,543 B2
(45) Date of Patent: Apr. 8, 2025

(54) SYSTEM AND METHOD FOR LOW-DOSE MULTI-PHASIC COMPUTED TOMOGRAPHY IMAGING OF THE KIDNEYS

(71) Applicant: WISCONSIN ALUMNI RESEARCH FOUNDATION, Madison, WI (US)

(72) Inventor: Andrew Wentland, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 304 days.

(21) Appl. No.: 17/866,796

(22) Filed: Jul. 18, 2022

(65) Prior Publication Data
US 2024/0016463 A1 Jan. 18, 2024

(51) Int. Cl.
*A61B 6/00* (2024.01)
*A61B 6/03* (2006.01)
(Continued)

(52) U.S. Cl.
CPC ............ *A61B 6/5205* (2013.01); *A61B 6/032* (2013.01); *A61B 6/4233* (2013.01); *A61B 6/463* (2013.01); *A61B 6/50* (2013.01); *A61B 6/542* (2013.01)

(58) Field of Classification Search
CPC ..... A61B 6/5205; A61B 6/032; A61B 6/4233; A61B 6/463; A61B 6/50; A61B 6/542;
(Continued)

(56) References Cited

U.S. PATENT DOCUMENTS 11,337,665 B2 * 5/2022 Maidment ............... A61K 47/02
2008/0025589 A1 * 1/2008 Ma ........................... G06T 7/11
382/131

(Continued)

OTHER PUBLICATIONS

Scheffel et al. "Dual-Energy Contrast-Enhanced Computed Tomography for the Detection of Urinary Stone Disease", Investigate Radiology, vol. 42, No. 12, Dec. 2007, p. 823-829. (Year: 2007).*

(Continued)

*Primary Examiner* — Dani Fox
*Assistant Examiner* — Mamadou Faye
(74) *Attorney, Agent, or Firm* — Quarles & Brady, LLP

(57) ABSTRACT

A system and method for creating multi-phase kidney computed tomography (CT) images of a patient are provided. The method includes acquiring or accessing CT data that includes a first dataset acquired from the patient during a first phase when a dose of a contrast agent is being excreted from a kidney of the patient and does not include a second dataset acquired from the patient during a second phase after the dose of the contrast agent is delivered but before the dose of a contrast agent is being excreted from a kidney. The method also includes using the first dataset, and without the second dataset, generating a set of multi-phase kidney images of the patient showing the patient prior to receiving the dose of the contrast agent, images showing the patient during the second phase following the dose of the contrast agent and before the dose of a contrast agent is being excreted from a kidney, and showing the patient during the first phase when the dose of a contrast agent is being excreted from a kidney of the patient. The method also includes communicating the multi-phase kidney images.

20 Claims, 5 Drawing Sheets

(51) Int. Cl.
  *A61B 6/42* (2024.01)
  *A61B 6/46* (2024.01)
  *A61B 6/50* (2024.01)

(58) Field of Classification Search
  CPC ... A61B 6/5217; A61B 6/4241; A61B 6/4441; A61B 6/482; A61B 6/481; A61B 5/201; A61B 2018/00511; A61B 6/507; A61B 6/03; G06T 2207/30084; G06T 2207/10081; G06T 2207/10072; A61M 2210/1082; A61P 13/12
  See application file for complete search history.

(56) References Cited

U.S. PATENT DOCUMENTS

2019/0192091 A1\* 6/2019 Lee .................. A61B 6/504
2024/0193777 A1\* 6/2024 Otani ................ G06T 7/0012

OTHER PUBLICATIONS

Jacobsen et al. "Multi-energy computed tomography and material quantification: Current barriers and opportunities for advancement", Medical Physics, 47 (8), Aug. 2020, p. 3752-3771). (Year: 2020).\*

\* cited by examiner

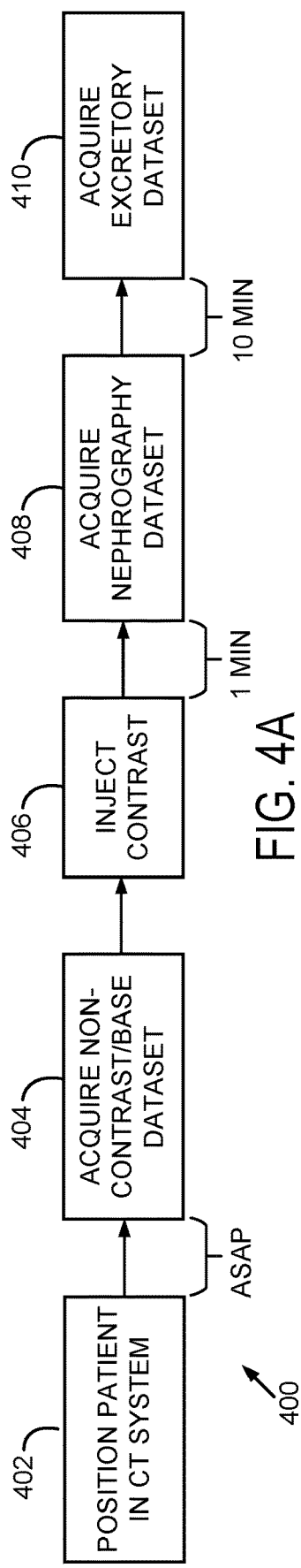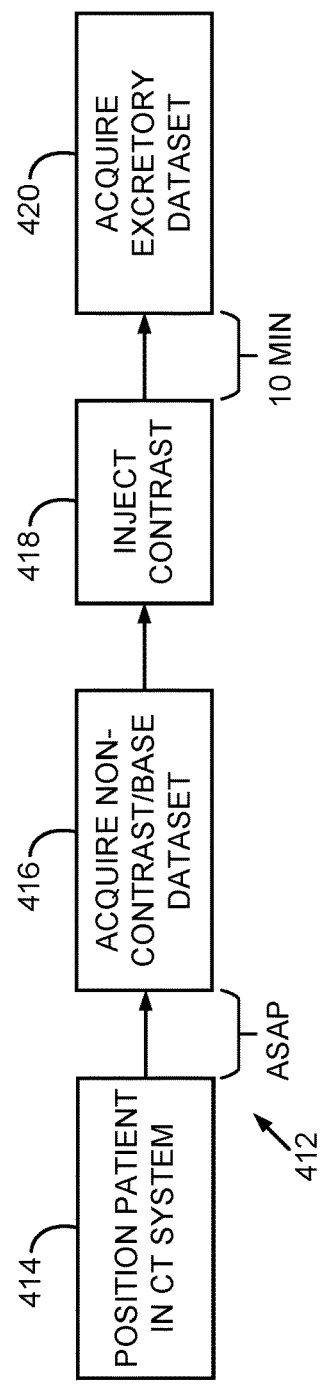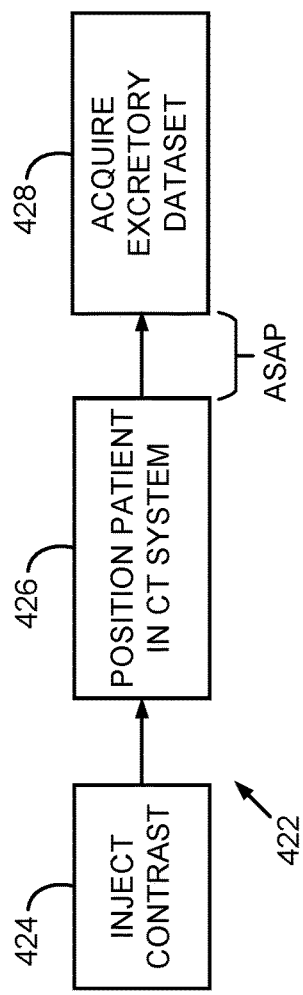
FIG. 4A - PRIOR ART -
FIG. 4B
FIG. 4C

SYSTEM AND METHOD FOR LOW-DOSE MULTI-PHASIC COMPUTED TOMOGRAPHY IMAGING OF THE KIDNEYS

CROSS-REFERENCE TO RELATED APPLICATIONS

N/A

STATEMENT REGARDING FEDERALLY SPONSORED RESEARCH

N/A

BACKGROUND

The present disclosure relates to systems and methods for medical imaging. More particularly, systems and method are provided for producing clinical multi-phasic images using computed tomography (CT) data that results in low or reduced radiation doses compared to traditional multi-phasic studies using CT imaging.

In computed tomography systems, an x-ray source projects a beam that is collimated to lie within an X-Y plane of a Cartesian coordinate system, termed the "imaging plane." The x-ray beam passes through the object being imaged, such as a medical patient, and impinges upon an array of radiation detectors. The intensity of the radiation received by each detector element is dependent upon the attenuation of the x-ray beam by the object and each detector element produces a separate electrical signal that relates to the attenuation of the beam. The linear attenuation coefficient is the parameter that describes how the intensity of the x-rays changes when passing through an object. The attenuation measurements from all the detectors are acquired to produce the transmission map of the object.

The source and detector array in a conventional CT system are rotated on a gantry within the imaging plane and around the object so that the projection angle at which the x-ray beam intersects the object constantly changes. A group of x-ray attenuation measurements from the detector array at a given angle is referred to as a "view" and a "scan" of the object. These views are collected to form a set of views made at different angular orientations during one or several revolutions of the x-ray source and detector. In a two-dimensional (2D) scan, data are processed to construct an image that corresponds to a 2D slice taken through the object. The prevailing method for reconstructing an image from 2D data is referred to in the art as the filtered back-projection (FBP) technique. This process converts the attenuation measurements from a scan into integers called "CT numbers" or "Hounsfield units," which are used to control the brightness of a corresponding pixel on a display.

Over the past 15 years, much effort has been committed to lowering radiation dose for x-ray CT imaging due to the potential cancer risks associated with the use of ionizing radiation in CT. Many efforts have been made to develop and commercialize systems and methods that enable low-dose CT imaging. Primarily, this has yielded noise-reduction algorithms that seek to compensate for the inevitable decreases in signal-to-noise ratio (SNR) that result when reduced dose is delivered on a given imaging acquisition. Unfortunately, many clinical applications require multiple, sequenced imaging acquisitions, which means that the patient receives multiple, successive radiation doses that must all yield sufficient SNR to meet clinical needs. Thus, in many clinical settings, slight dose reductions achieved with noise mitigation algorithms are of limited benefit.

Thus, it would be desirable to have systems and methods for providing CT images that are clinically-required for a given clinical application, while reducing the radiation dose experienced by the patient.

SUMMARY

The present disclosure provides systems and methods that overcome the aforementioned drawbacks by providing systems and methods for providing a set of multi-phase kidney CT image sets using fewer imaging acquisitions than the number of phases reflected in the resulting imaging series. For example, the systems and methods provided herein can deliver the three distinct image sets reflecting each phase of a 3-phase CT urography study using only one dual-energy CT acquisition (in the delayed/excretory/urographic/pyelographic phase) or two separate single-energy spectra CT acquisitions (in the non-contrast and delayed/excretory/urographic/pyelographic phases).

In accordance with one aspect of the disclosure, a method is provided for creating multi-phase kidney computed tomography (CT) images of a patient. The method includes acquiring or accessing CT data that includes a first dataset acquired from the patient during a first phase when a dose of a contrast agent is being excreted from a kidney of the patient and does not include a second dataset acquired from the patient during a second phase after the dose of the contrast agent is delivered but before the dose of a contrast agent is being excreted from a kidney. The method also includes using the first dataset, and without the second dataset, generating a set of multi-phase kidney images of the patient showing the patient prior to receiving the dose of the contrast agent, images showing the patient during the second phase following the dose of the contrast agent and before the dose of a contrast agent is being excreted from a kidney, and showing the patient during the first phase when the dose of a contrast agent is being excreted from a kidney of the patient. The method also includes communicating the multi-phase kidney images.

In accordance with another aspect of the disclosure, a medical imaging system is provided that includes an x-ray source configured to deliver x-rays to a patient as the x-ray source is rotated about the patient, a detector having a plurality of detector elements configured to receive the x-rays and generate sinogram data therefrom, and a controller configured to control the x-ray source to deliver the x-rays and to receive the sinogram data from the detector. The system also includes a processor configured to acquire CT data using the x-ray source and detector that includes an excretory dataset acquired from the patient during an excretory phase following a dose of a contrast agent and does not include a nephrographic dataset acquired from the patient during a nephrographic phase following the dose of the contrast agent. The processor is further configured to, using the excretory dataset and without any nephrographic dataset acquired from the patient during a nephrographic phase following the dose of the contrast agent, generate a set of multi-phase kidney images of the patient including baseline images showing the patient prior to receiving the dose of the contrast agent, nephrographic images showing the patient during the nephrographic phase following the dose of the contrast agent, and excretory images showing the patient during the excretory phase following the dose of the contrast agent. The system further includes a display configured to display the multi-phase kidney images.

In accordance with one other aspect of the disclosure, a computer system is provided including a non-transitory computer-readable storage medium that, when accessed by a processor, causes the processor to perform steps that include accessing only one dual-energy CT dataset or only two single-energy CT datasets and using the only one dual-energy CT dataset or only two single-energy CT datasets, generating three datasets. Each dataset in the three datasets correspond to one of a non-contrast phase, a nephrographic phase, and an excretory phase of a three-phase multi-phase kidney study. The processor is further caused to perform steps that include accessing respective non-contrast images generated from the dataset corresponding to the non-contrast phase, nephrographic images from the dataset corresponding to the nephrographic phase, and excretory images from the dataset corresponding to the excretory phase, and displaying the non-contrast images, the nephrographic images, and the excretory images.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 4A is a process diagraph of a traditional multiphase CT kidney imaging study.

FIG. 4B is a process diagraph of a multiphase CT kidney imaging study in accordance with the present disclosure using single-energy spectra CT acquisition datasets.

FIG. 4C is a process diagraph of an imaging study in accordance with the present disclosure using a dual-energy CT acquisition dataset.

DETAILED DESCRIPTION

Figure 1:
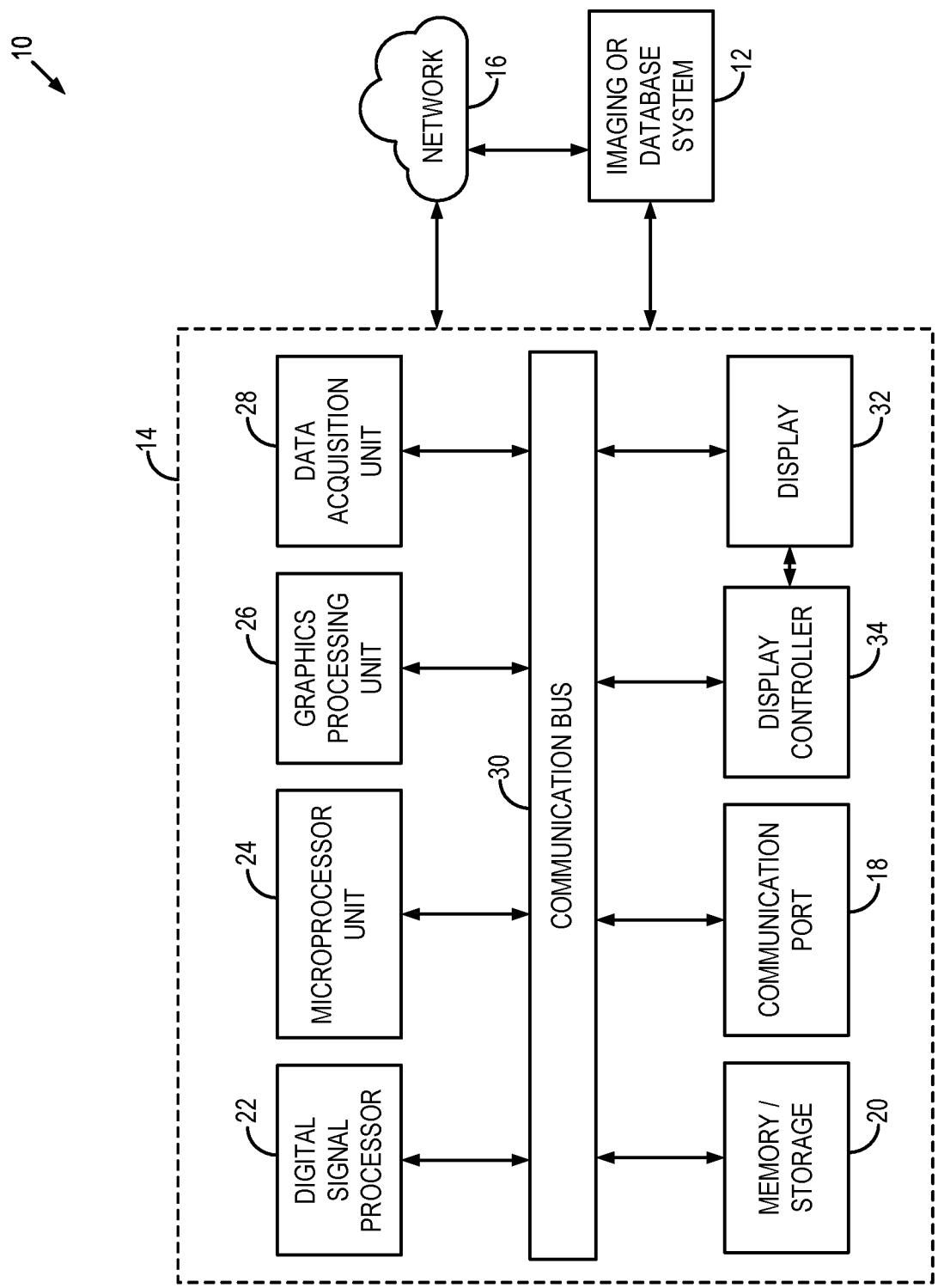
FIG. 1 is a schematic diagram of an example computer system that can be configured to implement the methods described herein.

The abdomen is a common area of patients imaged using computed tomography ("CT") imaging systems. For example, many vital organs and systems reside primarily within the abdomen. Many abdominal CT studies are performed in a single phase. For example, many single-phase CT studies are coordinate to peak portal venous blood flow. However, multi-phase CT acquisitions are preferred or required in certain clinical situations. Of course, as the duration of the CT study is extended, typically, so is the radiation dose experienced by the patient. When imaging the abdomen, the patient is receiving a radiation dose to the many organs and systems arranged therein.

CT imaging of the kidneys over multiple functional phases (i.e., multiphase kidney CT imaging) is an important clinical use of CT imaging to assist with the diagnosis and treatment of a wide variety of clinical indications. CT urography is one example of a clinical application that has required a multi-phase CT technique. CT urography is used clinically in the evaluation of hematuria, which can be caused by stones, infection, renal masses, or urothelial tumors. Initially, in a conventional 3-phase CT urography study, non-contrast (i.e. baseline) images are acquired to evaluate for stones and also to establish a baseline for potential tumor enhancement on subsequent CT phases. Secondly, a scan is repeated 90-100 seconds after the intravenous administration of iodinated contrast. This temporal delay allows for imaging of the nephrographic phase of the kidney. Thus, this second imaging phase is often referred to as the nephrographic phase acquisition, nephrographic phase, or nephrographic acquisition. Then, a third scan is acquired 5-15 minutes after the initial contrast injection, which allows for imaging of the pyelographic phase, when contrast has been excreted into the renal collecting system. Thus, this third imaging phase is often referred to as the pyelographic phase acquisition, pyelographic phase, or pyelographic acquisition. This third phase is also often referred to as a delayed phase, excretory phase, or urographic phase. Each of these three phases provides unique information about the kidney and collecting systems, and each are invaluable in the workup of hematuria. However, this conventional CT urography technique requires approximately 3× the radiation dose of a standard portal-venous-phase CT.

CT urography is only one non-limiting example of a kidney imaging application that extends over multiple phases. There are several different multi-phasic kidney CT examinations. Furthermore, there are alternative approaches for CT urography, such as acquiring the middle phase around 60 seconds after the injection of contrast, which is thus termed the "urothelial phase." Another form of multi-phase kidney CT is a renal mass protocol scan, which is another non-limiting example of a multi-phase kidney study or multi-phase kidney imaging protocol to which the systems and methods described herein can be readily applied. Such renal mass protocols can be three or four phases, and include a non-contrast (i.e. baseline) examination before the administration of contrast, corticomedullary and/or nephrographic phases following the administration of contrast, and a delayed phase, typically around two minutes following the administration of contrast.

As will be described, the present disclosure provides systems and methods that substantially reduce the radiation dose experienced by the patient during a CT kidney study, while still providing the desired multi-phase images. In one non-limiting example, the systems and methods provided herein can provide baseline images, nephrographic images, and pyelographic images of a urography study at the clinically-required image quality, while substantially reducing the overall radiation dose received by the patient. In one, non-limiting example, the systems and methods provided herein can synthesize diagnostic-quality nephrographic phase images without a dedicated nephrographic phase as part of the CT kidney data sets. Rather, in accordance with one example of the present disclosure, the nephrographic images can be generated from data acquired without a dedicated nephrographic acquisition. That is, in this non-limiting example, the nephrographic phase acquisition can be eliminated—effectively reducing the CT kidney acquisition from a three-phase to a two-phase study and, thus, reducing radiation dose by 33%. As will be described, in some configurations, the dose can be reduced further, for example, by approximately 66%. In another non-limiting example, the systems and methods provided herein can provide other pre- and post-contrast phases of the kidney, as desired or dictated by the clinical application.

Referring now to FIG. 1, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging or database (e.g., PACS) systems 12 or a variety of medical imaging systems. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a storage device. Alternatively, the medical imaging data may be provided by a PACS system or image database 12. To this end, the computer system 14 may include a communications port or other input port 18 for communication with the network 16 and system coupled thereto. Also, the computer system 14 may include memory and storage capacity 20 to store and access data or images.

In some configurations, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26. If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or a hardwire used for switching data between the peripherals or between any component, such as the communication buses described above.

The computer system 14 may also include or be connected to a display 32. To this end, the computer system 14 may include a display controller 34. The display 32 may be a monitor connected to the computer system 14 or may be integrated with the computer system 14, such as in portable computers or mobile devices.

Figure 2A:
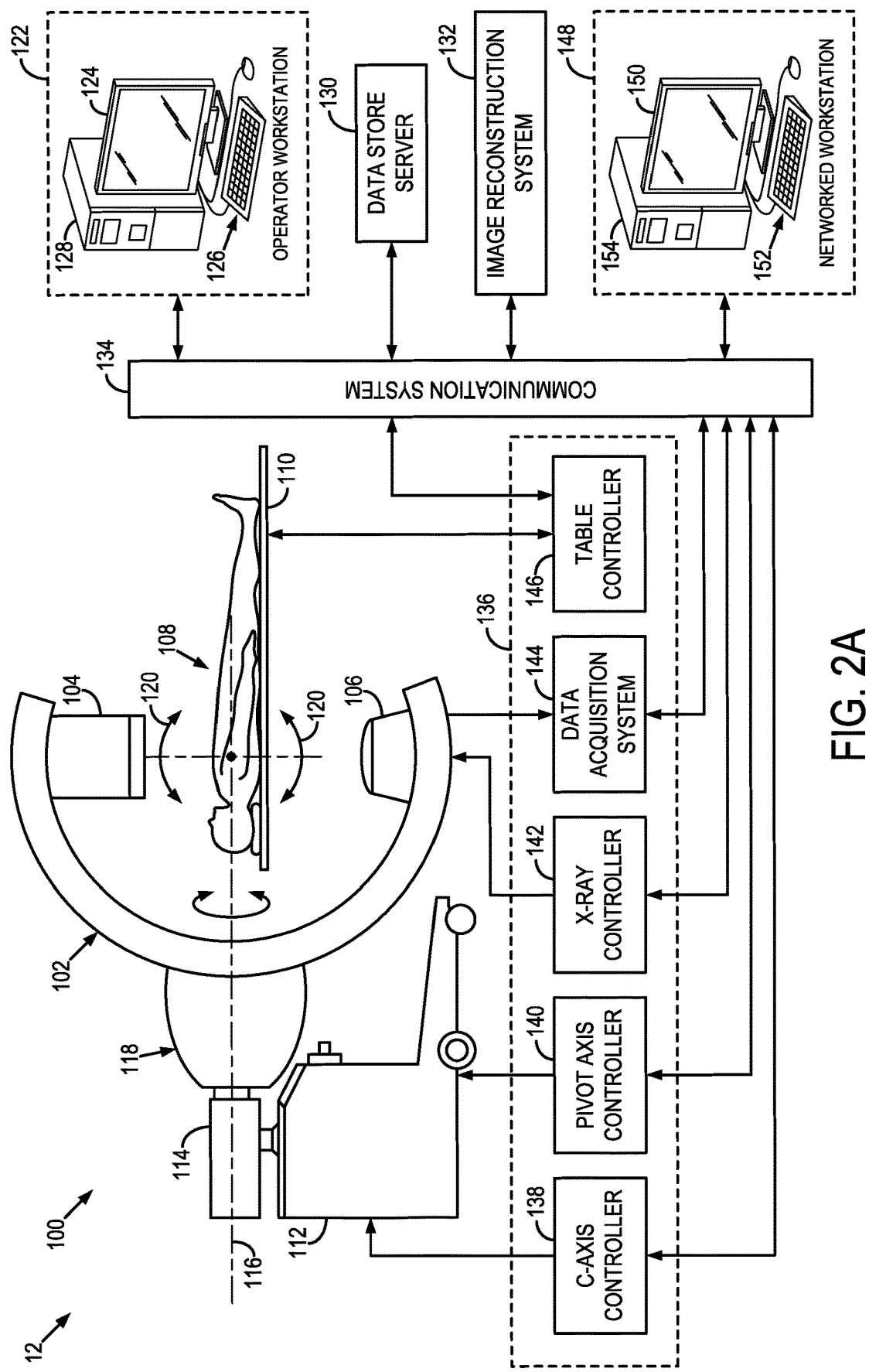
FIG. 2A is a schematic diagram of a C-arm x-ray computed tomography (CT) imaging system configured in accordance with the present disclosure.
Figure 2B:
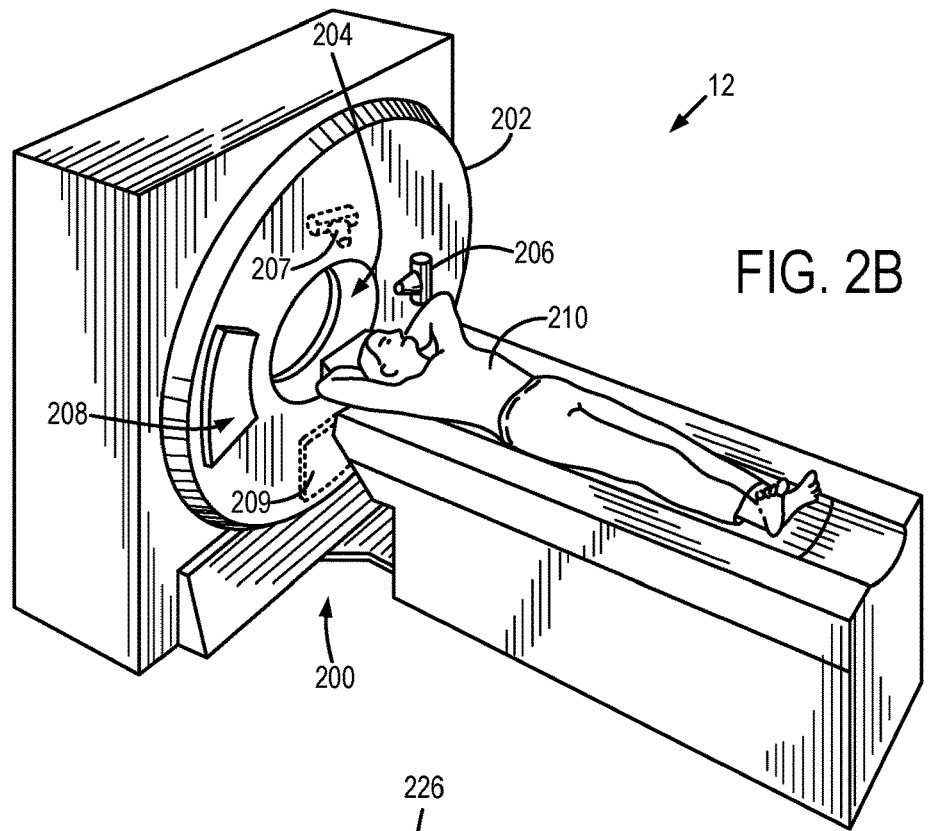
FIG. 2B is a perspective view of an example of an x-ray computed tomography (CT) system configured in accordance with the present disclosure.

Referring to FIG. 2A, one, non-limiting example of the imaging system 12 of FIG. 1 is provided. Specifically, in this example, a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems 200, such as illustrated in FIG. 2B, which may also serve as an example of the imaging system 12 of FIG. 1.

Referring again to FIG. 2A, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store server 130, and image reconstruction system 132 may be connected via a communication system 134, which may include any suitable network connection, whether wired, wireless, or a combination of both. As an example, the communication system 134 may include both proprietary or dedicated networks, as well as open networks, such as the Internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system (DAS) 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data are communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol (TCP), the Internet protocol (IP), or other known or suitable protocols.

Figure 2C:
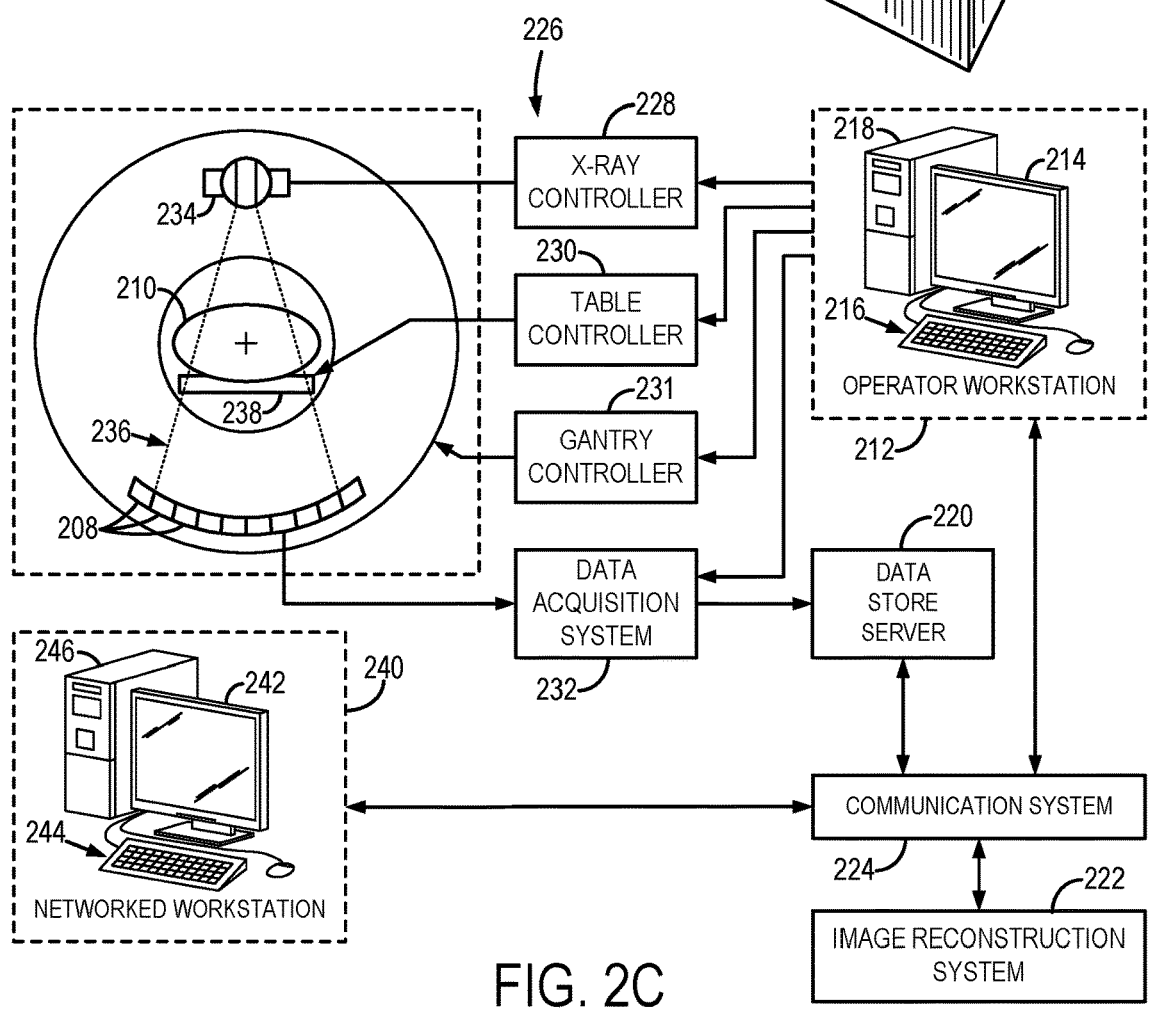
FIG. 2C is a block diagram of CT system, such as illustrated in FIG. 2B.

Similarly, referring to FIGS. 2B and 2C, the imaging system 12 may include a traditional CT system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210.

As illustrated in FIG. 2B, the CT system 200 may have a second x-ray source 207 and a second detector array 209. In this non-limiting example, the CT system 200 may be a dual-energy CT system that utilizes two x-ray sources 206, 207 and corresponding detectors 208, 209. As illustrated, the second x-ray source 207 and second detector 209 is optional. Furthermore, instead of a "switching" dual-energy source 207, the source may be a polychromatic source capable of yielding multi-energy x-ray data, such as described in U.S. Pat. No. 9,173,624, which is incorporated herein by reference. The CT system 200 may operate as a dual-energy imaging system with only the first x-ray source 206 and first x-ray detector 208, such as operating the first x-ray source 206 as an energy switching x-ray source.

The CT system 200 includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store server 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data are communicated from the DAS 232 to the data store server 220. The image reconstruction system 222 then retrieves the x-ray data from the data store server 220 and reconstructs an image therefrom. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

Figure 3:
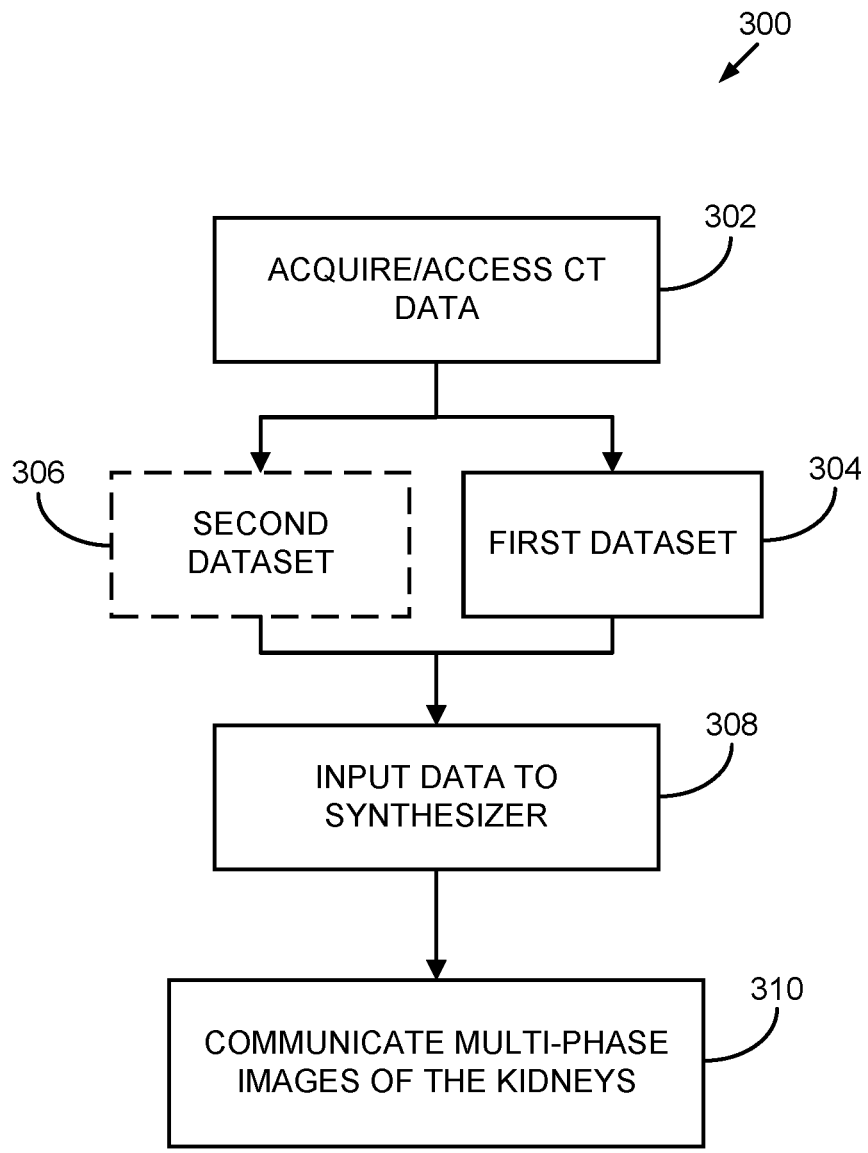
FIG. 3 is a flow chart setting forth some example steps of a process in accordance with the present disclosure.

Referring to FIG. 3, the system of FIG. 1 may carry out a process 300 for creating a clinical, multi-phase kidney image set. The process that will be described may be applied to a variety of multi-phase kidney imaging protocols. Regardless of the clinical protocol or the underlying purpose of the study, the process includes acquiring at least some CT datasets from the patient as the kidney is in at least one phase of processing a contrast agent. In one, non-limiting example, the multi-phase kidney study may be a urography image study, which is defined to include (1) non-contrast or baseline images, (2) nephrographic images, and (3) excretory (i.e. delayed/urographic/pyelographic) images. The specific names for the multiple phases may vary by clinical setting or purpose. However, irrespective of the names for each phase or the purpose for acquiring data from a given phase, as will be described, the systems and methods provided herein allows the creation of images covering multiple phases, when CT data was acquired from less than all of the phases reflected in the final images. As one non-limiting example, as noted above, irrespective of name, a urography image study may yield three image sets, one for each of the three phases. In accordance with the systems and methods provided in the present disclosure, all three images sets (baseline, nephrographic, and excretory) of a urography image study can be generated from the acquisition of less than three image datasets. In the following, non-limiting example, reference to particular numbers of phases or particular names for particular phases is not necessarily limiting, but just one example.

Referring to FIG. 3, at process block 302, the process 300 begins with acquiring or accessing CT data. The CT data may be stored data, such as accessible via a PACS or other image storage and retrieval system, or may be acquired using a CT system, such as described above. The data includes a first dataset reflected by process block 304 and, optionally, may include a second dataset reflected by process block 306. Each dataset 304, 306 may include data acquired from a particular phase of a multi-phase kidney study. To this end, optionally, the data may include additional datasets corresponding to additional phases. That is, the present example will be described with respect to a 3-phase kidney study, which in accordance with the present disclosures can use the first dataset 304 and the option second dataset 306, but need not be limited to only 3 phases.

More particularly, the CT data may be single-energy or dual-energy CT data. In the case of single-energy CT data, both of the two datasets 304, 306 may be acquired or accessed, whereby the first dataset 304 correspond to a first phase and the second dataset 306 corresponds to a second phase. In the non-limiting example of a urography study, the first dataset 304 may have been acquired during an excretory (i.e. delayed/urographic/pyelographic) phase showing the kidney of the patient excreting a contrast agent that was delivered to the patient. Furthermore, the second dataset 306 may have been acquired during a baseline phase showing the kidneys before the patient received the contrast agent. Thus, in the case of single-energy CT data acquired for a urography study, no nephrographic dataset is included in the CT data at process block 302.

In the case of dual-energy CT data for a urography study, only the first dataset 304 is utilized, which was acquired during an excretory phase. Thus, in the case of dual-energy CT data for a urography study, no baseline or nephrographic dataset is included in the CT data at process block 302.

This stands in stark contrast to traditional urography CT datasets. For example, referring to FIG. 4A, a process 400 for acquiring a traditional urography dataset for producing urography images starts by placing the patient in the CT system at process block 402. Immediately thereafter, a non-contrast or baseline dataset is acquired at process block 404. Thereafter, the patient receives a dose of contrast at process block 406. After delivering the contrast at process block 406 a nephrographic (or corticomedullary, urothelial, or other post-contrast phases) dataset is acquired at process block 408. In one non-limiting example, this may occur approximately 45-100 seconds (depending on the parameters of the CT urography protocol) after delivering the contrast at process block 406. As another non-limiting example, the nephrographic (or corticomedullary, urothelial, or other post-contrast phases) dataset may be acquired between 30 and 120 seconds after the injection of contrast phase depending on timing. After a duration selected based on the parameters of the CT urography protocol to allow the contrast wash-through to reach the excretory phase, a third imaging acquisition is performed to acquire the excretory (i.e. delayed, pyelographic, urographic, or related terminology) dataset at process block 410. In one, non-limiting example, this timing may be approximately 2-15 minutes after contrast injection. Thus, in the traditional urography imaging process, three separate CT imaging sessions (one to acquire the baseline dataset 404, one to acquire the nephrographic (or corticomedullary, urothelial, or other post-contrast phases acquired between 30 and 120 seconds after the injection of contrast) dataset 408, and one to acquire the excretory (i.e. delayed, pyelographic, urographic, or related terminology) dataset 410) with three associated radiation doses are performed relative to the patient.

In accordance with the present disclosure, as described, at least one of the imaging sessions and associated radiation doses can be removed, while still providing the requisite multi-phase image sets that form a clinical multi-phase kidney image set. In one non-limiting example, in the context of a urography imaging study, the present disclosure provides systems and methods for creating three image sets (baseline, nephrographic, and excretory) from just two or even a single dataset, which thereby substantially reduces the radiation dose to the patient, as well as the overall imaging/room time for the patient.

For example, referring to FIG. 4B, a process 412 for acquiring data for a clinical, multi-phase kidney image set using a single-energy CT acquisition in accordance with the present disclosure is provided. The process 412 begins with positioning the patient in the CT system at process block 414 and then immediately acquiring a non-contrast/baseline dataset at process block 416. Thereafter, the patient receives a dose of contrast at process block 418. However, in accordance with the present disclosure, no imaging session is performed to acquire a nephrographic (or urothelial or corticomedullary) dataset. Instead, after a delay, for example of approximately 2-15 minutes, only an excretory (i.e. delayed, pyelographic, urographic, or related terminology) dataset is acquired at process block 420. Thus, in the non-limiting application of urography imaging, the present disclosure enables the traditional urography imaging process 400 of FIG. 4A to be reduced into only two steps of data acquisition 416, 420, instead of three (404, 408, 410), thereby reducing the radiation dose to the patient by 33 percent.

Further still, referring to FIG. 4C, a process 422 for acquiring data for a clinical, multi-phase kidney image set using a dual-energy CT acquisition in accordance with the present disclosure is provided. The process 422 begins with injecting the patient with contrast at process block 424. Thereafter, the patient is positioned in the CT system at process block 426. In this way, as the patient is being positioned, the contrast moves through the patient and, once positioned, the process immediately moves to acquiring only an excretory (i.e. delayed, pyelographic, urographic, or related terminology) dataset at process block 428. Thus, in the non-limiting application of urography imaging, the present disclosure enables the traditional urography imaging process 400 of FIG. 4A to be reduced into only a single data acquisition 428, instead of three (404, 408, 410), thereby reducing the radiation dose to the patient by approximately 66 percent and reducing the overall imaging time from approximately 15 minutes in the process of FIG. 4A to approximately 2-5 minutes in the process of FIG. 4C.

Thus, referring again to FIG. 3, the acquired/accessed CT data at process block 302 may include only the first dataset 304 if the dataset is a dual-energy dataset, which may correspond to an excretory dataset. Alternatively, if the dataset is a single-energy dataset, only the first dataset 304 (for example, corresponding to the excretory phase) and the second dataset 306 (corresponding to a baseline or non-contrast phase) may be acquired or accessed at process block 302. In either case, at process block 308, the data is provided to a synthesizer in accordance with the present disclosure to generate a set of multi-phase images of the kidneys that is communicated at process block 310, such as displayed.

In the non-limiting example of a 3-phase urography study, the synthesizer is built to utilize information available in baseline and/or excretory datasets to create additional images that typically require additional acquisitions to generate. That is, the present disclosure recognizes that the biological half-life of iodinated contrast agents is 30-minutes in subjects with normal renal function and substantially longer in those with impaired renal function. Therefore, images acquired during the excretory (i.e. delayed, pyelographic, urographic, or related terminology) phase at 2-15 minutes post-injection also contain information about the corticomedullary, urothelial, and nephrographic phases as the contrast is continually processed by the kidneys. Thus, the synthesis of nephrographic (or corticomedullary, urothelial, or other post-contrast phases acquired between 30 and 120 seconds after the injection of contrast) phase images is achievable due to, for example, the redundancy of information contained within the excretory (i.e. delayed, pyelographic, urographic, or related terminology) phase images. Thus, the present disclosure reduces the number of acquisitions and, accordingly the radiation dose, required to generate clinical, multi-phase kidney image sets using an image synthesizer.

The synthesizer may be designed to synthesize nephrographic (or corticomedullary, urothelial, or other post-contrast) phase images from single- or dual-energy CT kidney datasets. In accordance with one non-limiting example, the synthesizer may utilize an artificial intelligence model. The artificial intelligence model may be trained using excretory (i.e. delayed, pyelographic, urographic, or related terminology) phase images from dual-energy CT kidney studies and virtual non-contrast images created from the dual-energy acquisition. That is, in accordance with the present disclosure, an image synthesizer has been developed that produces images that were not actually acquired, namely the nephrographic (or corticomedullary, urothelial, or other post-contrast phases) images. In doing so, the synthesizer substantially reduces the radiation dose required for multi-phasic clinical CT kidney examinations. Dual-energy CT allows for the creation of virtual non-contrast images. Advantageously, virtual non-contrast images are inherently registered to the acquired images. As such, an artificial intelligence model may be trained to synthesize nephrographic (or corticomedullary, urothelial, or other post-contrast phases) images using the excretory (i.e. delayed, pyelographic, urographic, or related terminology) images and the virtual non-contrast images. Thus, only a single dual-energy acquisition of the excretory (i.e. delayed, pyelographic, urographic, or related terminology) phase is ultimately needed, leading to a ~66% radiation dose reduction compared to the traditional 3-phase acquisition. Thus, the synthesizer may utilize or include an artificial intelligence model that is trained to synthesize nephrographic (or corticomedullary, urothelial, or other post-contrast phases) images using the excretory (i.e. delayed, pyelographic, urographic, or related terminology) images and the virtual non-contrast images.

The synthesizer may be created using an artificial intelligence system, which may be trained using baseline and excretory (i.e. delayed, pyelographic, urographic, or related terminology) datasets/images as inputs. In the case of dual-energy CT datasets, the baseline or non-contrast datasets/images may be virtual baseline or non-contrast datasets/images. The artificial intelligence system receives those inputs and generates the nephrographic (or corticomedullary, urothelial, or other post-contrast phases) images. During training of this artificial intelligence system, the generated nephrographic (or corticomedullary, urothelial, or other post-contrast phases) images are compared to a ground truth, which may be an actual nephrographic (or corticomedullary, urothelial, or other post-contrast phases acquired between 30 and 120 seconds after the injection of contrast) image acquired from the patient during the nephrographic (or corticomedullary, urothelial, or other post-contrast phases) phase. From this comparison with ground truth, the artificial intelligence system may be further trained using the differences between the generated nephrographic (or corticomedullary, urothelial, or other post-contrast phases) images and the ground truth images. The artificial intelligence system may operate in a discrete training mode and then may be utilized clinically. Additional and optionally, the artificial intelligence system may continue to learn from feedback in clinical settings, for example feedback from clinicians regarding the nephrographic (or corticomedullary, urothelial, or other post-contrast phases) images that are generated.

The systems and methods described above can be applied in a variety of multi-phase kidney imaging applications, which includes but is not limited to CT urography and 3- or 4-phase renal mass protocol CT examinations. For example, hematuria is a common concern and can be caused by many conditions, such as kidney stones; tumors in the kidneys; tumors in the collecting systems, ureters, and bladder; blood clots; infection; and the like. CT urography is a common technique for evaluating hematuria.

As used herein, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for creating multi-phase kidney computed tomography (CT) images of a patient comprising:
   acquiring or accessing CT data that includes a first dataset acquired from the patient during a first phase when a dose of a contrast agent is being excreted from a kidney of the patient and does not include a second dataset acquired from the patient during a second phase after the dose of the contrast agent is delivered but before the dose of a contrast agent is being excreted from a kidney;
   using the first dataset and without the second dataset, generating a set of multi-phase kidney images of the patient showing the patient prior to receiving the dose of the contrast agent, images showing the patient during the second phase following the dose of the contrast agent and before the dose of a contrast agent is being excreted from a kidney, and images showing the patient during the first phase when the dose of a contrast agent is being excreted from a kidney of the patient; and
   communicating the multi-phase kidney images.

2. The method of claim 1 wherein accessing or acquiring the CT data includes accessing or acquiring (i) a single-energy baseline CT dataset acquired from the patient before the dose of the contrast agent and a single-energy excretory CT dataset acquired from the patient during the first phase or (ii) a dual-energy excretory CT dataset acquired from the patient during the first phase.

3. The method of claim 2, wherein generating the set of multi-phase kidney images includes reconstructing the single-energy baseline CT dataset and the single-energy CT dataset acquired from the patient during the first phase into the baseline images and excretory images and using the single-energy baseline CT dataset and the single-energy CT dataset acquired from the patient during the first phase to generate images showing the patient during the second phase.

4. The method of claim 3, wherein using the single-energy baseline CT dataset and the single-energy excretory CT dataset to generate the images showing the patient during the second phase includes delivering the single-energy baseline CT dataset and the single-energy excretory CT dataset to a trained, artificial intelligence module configured to generate the images showing the patient during the second phase.

5. The method of claim 2, wherein generating the set of multi-phase kidney images includes reconstructing the dual-energy excretory CT dataset into the excretory images, generating virtual baseline images showing the patient before receiving the contrast agent, and generating the images showing the patient during the second phase.

6. The method of claim 5, wherein generating the images showing the patient during the second phase includes delivering the dual-energy excretory CT dataset to a trained, artificial intelligence module configured to generate the images showing the patient during the second phase from the dual-energy excretory CT dataset and the virtual baseline images.

7. The method of claim 1, wherein communicating the multi-phase kidney images includes displaying at least one of each of images showing the patient before receiving a dose of the contrast agent, images showing the patient during the second phase, and images showing the patient during the first phase.

8. A medical imaging system comprising:
   an x-ray source configured to deliver x-rays to a patient as the x-ray source is rotated about the patient;
   a detector having a plurality of detector elements configured to receive the x-rays and generate sinogram data therefrom;
   a controller configured to control the x-ray source to deliver the x-rays and to receive the sinogram data from the detector;
   a processor configured to:
     acquire CT data using the x-ray source and detector that includes an excretory dataset acquired from the patient during an excretory phase following a dose of a contrast agent and does not include a nephrographic dataset acquired from the patient during a nephrographic phase following the dose of the contrast agent;
     using the excretory dataset and without any nephrographic dataset acquired from the patient during a nephrographic phase following the dose of the contrast agent, generate a set of multi-phase kidney images of the patient including baseline images showing the patient prior to receiving the dose of the contrast agent, nephrographic images showing the patient during the nephrographic phase following the dose of the contrast agent, and excretory images showing the patient during the excretory phase following the dose of the contrast agent; and
   a display configured to display the multi-phase kidney images.

9. The system of claim 8 wherein acquiring the CT data includes acquiring (i) a single-energy baseline CT dataset and a single-energy excretory CT dataset or (ii) a dual-energy excretory CT dataset.

10. The system of claim 9, wherein generating the set of multi-phase kidney images includes reconstructing the single-energy baseline CT dataset and the single-energy excretory CT dataset into the baseline images and the excretory images and using the single-energy baseline CT dataset and the single-energy excretory CT dataset to generate the nephrographic images showing the patient during the nephrographic phase following the dose of the contrast agent.

11. The system of claim 10, wherein using the single-energy baseline CT dataset and the single-energy excretory CT dataset to generate the nephrographic images showing the patient during the nephrographic phase following the dose of the contrast agent includes delivering the single-energy baseline CT dataset and the single-energy excretory CT dataset to a trained, artificial intelligence module configured to generate the nephrographic images showing the patient during the nephrographic phase following the dose of the contrast agent from the single-energy baseline CT dataset and the single-energy excretory CT dataset.

12. The system of claim 9, wherein generating the set of multi-phase kidney images includes reconstructing the dual-energy excretory CT dataset into the excretory images, generating virtual baseline images showing the patient before receiving the contrast agent, and generating the nephrographic images showing the patient during the nephrographic phase following the dose of the contrast agent from the dual-energy excretory CT dataset.

13. The system of claim 12, wherein generating the nephrographic images includes delivering the dual-energy excretory CT dataset and the virtual baseline images to a trained, artificial intelligence module configured to generate the nephrographic images showing the patient during the nephrographic phase following the dose of the contrast agent from the dual-energy excretory CT dataset and the virtual baseline images.

14. The system of claim 8, wherein acquiring the CT data using the x-ray source and detector takes less than 5 minutes.

15. The system of claim 8, wherein acquiring the CT data using the x-ray source and detector takes less than 2 minutes.

16. A computer system including a non-transitory computer-readable storage medium that, when accessed by a processor, causes the processor to perform steps comprising:
accessing only one dual-energy CT dataset or only two single-energy CT datasets, wherein the only one dual-energy CT dataset or only two single-energy CT datasets do not include data acquired during a nephrographic phase of a multi-phase kidney study;
using the only one dual-energy CT dataset or only two single-energy CT datasets, generating three datasets that respectively correspond to a non-contrast phase, the nephrographic phase, and an excretory phase of the multi-phase kidney study;
accessing respective non-contrast images generated from the dataset corresponding to the non-contrast phase, nephrographic images from the dataset corresponding to the nephrographic phase, and excretory images from the dataset corresponding to the excretory phase; and
displaying the non-contrast images, the nephrographic images, and the excretory images.

17. The system of claim 16, wherein the only one dual-energy CT dataset is acquired during an excretory phase of a multi-phase kidney imaging study.

18. The system of claim 16, wherein a first of the only two single-energy CT datasets is acquired prior to a patient receiving a dose of contrast and a second of the only two single-energy CT datasets is acquired during an excretory phase of a multi-phase kidney imaging study.

19. The system of claim 16, wherein, to generate a set of three datasets, the computer is further caused to provide the only one dual-energy CT dataset or only two single-energy CT datasets to an artificial intelligence system to generate the dataset corresponding to the nephrographic phase.

20. The system of claim 16, wherein displaying the non-contrast images, the nephrographic images, and the excretory images includes communicating the non-contrast images, the nephrographic images, and the excretory images to a display system.

* * * * *

UNITED STATES PATENT AND TRADEMARK OFFICE
CERTIFICATE OF CORRECTION

PATENT NO. : 12,268,543 B2
APPLICATION NO. : 17/866796
DATED : April 8, 2025
INVENTOR(S) : Andrew Wentland Page 1 of 1

It is certified that error appears in the above-identified patent and that said Letters Patent is hereby corrected as shown below:

In the Specification

Column 11, Line 63, "30-minutes" should be --30-60 minutes--.

Signed and Sealed this
Thirteenth Day of May, 2025

Coke Morgan Stewart
*Acting Director of the United States Patent and Trademark Office*